United States Patent
Berger et al.

(10) Patent No.: US 7,678,937 B2
(45) Date of Patent: Mar. 16, 2010

(54) POLYALKYLATED ARYLALKYL SULFONIC ACIDS AND THEIR SALTS

(76) Inventors: Paul Daniel Berger, 3014 Deer Creek Dr., Sugar Land, TX (US) 77478; Christie H Berger, 3014 Deer Creek Dr., Sugar Land, TX (US) 77478; Guohua Cao, 4303 Round Tree La., Missouri City, TX (US) 77459; Oliver S Hsu, 4303 Round Tree La., Missouri City, TX (US) 77459

( * ) Notice: Subject to any disclaimer, the term of this patent is extended or adjusted under 35 U.S.C. 154(b) by 318 days.

(21) Appl. No.: 11/978,331

(22) Filed: Oct. 29, 2007

(65) Prior Publication Data

US 2009/0023950 A1    Jan. 22, 2009

Related U.S. Application Data

(60) Provisional application No. 60/959,943, filed on Jul. 18, 2007.

(51) Int. Cl.
*C07C 303/22* (2006.01)
(52) U.S. Cl. .................................................. 562/115
(58) Field of Classification Search .................. 562/115
See application file for complete search history.

(56) References Cited

U.S. PATENT DOCUMENTS

| | | | |
|---|---|---|---|
| 4,004,638 A | 1/1977 | Burdyn et al. | |
| 4,220,204 A | 9/1980 | Hughes et al. | |
| 4,536,301 A | 8/1985 | Malloy et al. | |
| 6,022,834 A | 2/2000 | Hsu et al. | |
| 6,043,391 A | 3/2000 | Berger et al. | |
| 7,256,306 B2 | 8/2007 | Dado et al. | |

FOREIGN PATENT DOCUMENTS

GB    22 32 428    6/1989

OTHER PUBLICATIONS

U.S. Appl. No. 11/895,497, filed Aug. 24, 2007, Berger et al.
Jiang et al, Synthesis of Unsymmetrical Bola Form Surfactants with a Sulfonate Group and a Carboxyl Group, J. Surfact Deterg (2007) 10: 131-136 Springer N.Y.

*Primary Examiner*—Peter G O'Sullivan

(57) ABSTRACT

The present invention discloses a process for producing light colored polyalkylated arylalkyl sulfonic acids. The polyalkylated arylalkyl sulfonic acids may be further neutralized with alkalis or amines to form the corresponding light colored sulfonated salts. The present invention also makes manufacture of polyalkylated arylalkyl sulfonic acids possible as first intent products using an inexpensive and simple reaction. The structure of the polyalkylated arylalkyl sulfonic acids produced using the process described in the present invention is shown below:

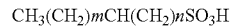

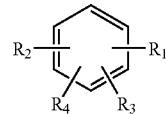

Where
$R_1$, $R_2$ and $R_3$ are each separately and independently H, alkyl (branched or linear C1 to C30),
$R_4 = CH_3(CH_2)oCH(CH_2)pCH_3$
m+n=4 to 28
o+p=3 to 27.

8 Claims, No Drawings

POLYALKYLATED ARYLALKYL SULFONIC ACIDS AND THEIR SALTS

CROSS REFERENCE TO RELATED APPLICATIONS

This application is based on provisional patent application Ser. No. 60/959,943 filed on Jul. 18, 2007.

FIELD OF THE INVENTION

The present invention relates to a process for producing higher molecular weight anionic surfactants. More particularly the present invention relates to a process for preparing light color dialkyl and higher substituted aromatic sulfonic acids and sulfonates using arylalkyl sulfonic acids and olefins that are preferred for certain industries.

Arylalkyl sulfonic acids are sulfonic acids where the sulfonate group is attached to one or more alkyl chains as defined in U.S. Pat. No. 6,043,391 as opposed to arylalkyl sulfonic acids where the sulfonate is attached to the aromatic ring.

The new process of the present invention for preparing the light color higher molecular weight poly substituted arylalkyl sulfonic acids and sulfonates, commonly known as heavy arylalkyl sulfonic acids and heavy arylalkyl sulfonates, has the following advantages over existing processes:

1. Di and higher substituted arylalkyl sulfonic acids and sulfonates can be produced easily in light color and high yields as a first intent product.
2. Light colored di and higher substituted arylalkyl sulfonic acid and sulfonates can be produced without using the costly, conventional alkylation processes.
3. Light colored di and higher substituted arylalkyl sulfonic acid and sulfonates can be produced without using the conventional costly and hazardous catalyst such as aluminum chloride ($AlCl_3$) or hydrofluoric acid (HF).
4. The light colored di and higher substituted arylalkyl sulfonic acids and sulfonates have superior solubility characteristics and lower viscosities than their existing alkylaryl sulfonic acid counterparts.
5. The process produces light color, high molecular weight polyalkylated sulfonic acid without the necessity of sulfonated high molecular weight, viscous alkylates.
6. Light colored, di and higher substituted arylalkyl sulfonic acids and their salts can be produced from a minimum number of raw materials at low cost and high yield.
7. Light colored di and higher substituted arylalkyl sulfonic acids and their salts can be produced with lower colors and greater purity than acids produced conventionally from high molecular weight (heavy) alkylaryl alkylate.
8. Heavy arylalkyl sulfonates have been shown to produce products with superior detergency, solubilities and electrolyte tolerance however their colors are no better than those for heavy alkylaryl sulfonates. The process of this invention produces heavy arylalkyl sulfonates with lighter colors while still maintaining all the superior qualities over alkylaryl sulfonates.

THE PRIOR ART

Berger et al. U.S. patent application Ser. No. 11/895,497 disclose a method where an arylalkyl sulfonic acid is reacted with an olefin to produce polyalkylated arylalkyl sulfonic acids and their salts. This process produces products having higher colors that restrict them from applications where color is of importance including but not restricted to personal care, pharmaceuticals, laundry, heavy duty cleaners. The process of the present invention offers a much simpler and effective method to synthesize these products as well as producing products with structures having better surface properties and solubility since the sulfonate group is on the alkyl chain and not the aromatic ring.

SUMMARY OF INVENTION

The present invention resides in an improved process for producing lighter color polyalkylated arylalkyl sulfonic acids and their sulfonates. Excess olefin in molar quantities of up to 100 percent of the amount used to produce olefin sulfonic acid is used during the sulfonation and the resulting olefin sulfonic acid and olefin is further reacted with aromatic compound or substituted aromatic compound to form a light color higher molecular weight polyalkylated arylalkyl sulfonic acid. This light color, higher molecular weight polyalkylated arylalkyl sulfonic acid can be further reacted with alkalis including but not limited to sodium hydroxide, sodium carbonate, potassium hydroxide, potassium carbonate, calcium hydroxide, magnesium hydroxide, or amines to form their corresponding sulfonate salts.

The present invention involves a process for the manufacture of light color polyalkylated arylalkyl sulfonic acids and their salts comprising:
a. sulfonating an olefin in the presence of excess olefin,
b. further reacting the olefin sulfonic acid formed with an aromatic or substituted aromatic to form an arylalkyl sulfonic acid,
c. allowing the arylalkyl sulfonic acid to further react with the excess olefin present to form polyalkylated arylalkyl sulfonic acid with the structure below:

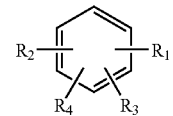

Where
$R_1$, $R_2$ and $R_3$ are each separately and independently H, alkyl (branched or linear C1 to C30),
$R_4$=$CH_3(CH_2)oCH(CH_2)pCH_3$
$m+n=4$ to 28
$o+p=3$ to 27,
d. optionally neutralizing the polyalkylated arylalkyl sulfonate with a base.

DETAILED DESCRIPTION OF THE INVENTION

The present invention uses olefin sulfonic acid produced by the thin film sulfonation containing excess olefin to produce the mixture of light color olefin sulfonic acid and the unreacted olefin. The resulting olefin sulfonic acid is further reacting with an aromatic compound or substituted aromatic compound, including, but not limited to benzene, naphthalene, toluene, xylene, ethyl benzene, to form arylalkyl sulfonic acid. The resulting arylalkyl sulfonic acid is then simultaneously alkylated with the excess olefin present to produce the corresponding polyaryl alkyl sulfonic acid having two alkyl groups, one derived from the alpha-olefin and the other from the excess olefin used during the reaction. Other olefins such as branched olefins may be used. The reaction is usually carried out in a falling film reactor Sulfonation technology is well known within the art. Excess olefin is used to under-sulfonate the olefin in the sulfonation process in order to obtain the light color acid that is required for certain industries. Furthermore, the excess olefin is to be used to form the polyalkylated sulfonic acid subsequently formed with the addition of aromatics or substituted aromatics with the structures shown in FIG. 1. The excess amount of olefin depends on the final mixture of the mono, di, and tri-arylalkyl sulfonic acid required. The excess olefin also serves as a solvent during the thin film sulfonation process, reducing the viscosity of the olefin sulfonic acid formed and also reducing the color of the final product and the residual sulfur trioxide.

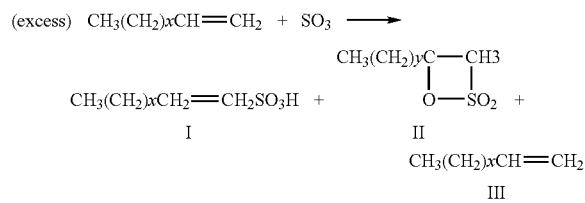

where:

x=3 to 27 y=3 to 27

The olefin sulfonic acid above that is a mixture of alkene sulfonic acid (I), sultone (II) and excess olefin (III) is reacted with an aromatic compound to form an arylalkyl sulfonic acid (structure IV below).

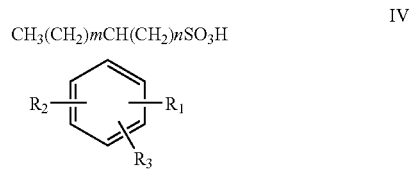

This arylalkyl sulfonic acid subsequently reacts with the excess olefin present to form a polyalkylated arylalkyl sulfonic acid (structure V) shown below.

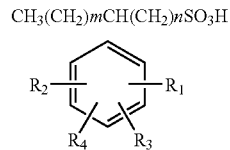

Where:

$R_1$, $R_2$ and $R_3$ are each separately and independently H, alkyl (branched or linear C1 to C30), $R_4$=$CH_3(CH_2)oCH(CH_2)pCH_3$ m+n=4 to 28 o+p=3 to 27

$R_4$=is an alkyl group having the same carbon number and carbon number distribution as the original starting olefin A catalyst has been found useful to reduce the reaction temperature, the reaction times and improve yields. Useful catalysts include but are not limited to sulfuric acid, methane sulfonic acid, sulfosuccinic acid, alkylaryl sulfonic acids, arylalkyl sulfonic acids including the reaction product itself, and other strong acid catalysts generally used for alkylation.

The catalyst is used at concentrations below 25% of the initial amount of alpha olefin sulfonic acid, usually from 1 to 20%. The exact amount of catalyst used depends on the olefin sulfonic acid, the aromatics and the substituted aromatics, and the reaction temperature. Higher temperatures, up to the decomposition temperatures of the reactants are preferred. Pressure may be necessary to reach the desired higher temperatures when using low boiling starting materials such as benzene. Unexpectedly we have found that the use of sulfonated arylalkyl sulfonic acids containing an excess of unreacted olefin allows the olefin to easily attach itself to the aromatic ring of the arylalkyl sulfonic acid resulting in high yields of low color poly arylalkyl sulfonic acids (structure V) and very little unreacted olefin and little or no sulfuric acid. The sulfuric acid is formed when residual sulfur trioxide from the thin film reaction contacts water. The process of this invention contain very slight to none of the excess of the sulfur trioxide therefore, very slight to none of the sulfuric acid is formed as in contrast to the results obtained when a conventional alkylaryl sulfonic acid such as alkylbenzene sulfonic acid is combined with an olefin. In this case no reaction was observed.

The starting olefins may be linear or branched and from C6 to C30 carbons in length. Alpha-olefins (AO) as well as internal olefins (IO) may be used. Mixtures of more than one olefin may be used.

This reaction is carried out at temperatures between 40° C. and 200° C., preferably between 80° C. and 140° C., using approximately equimolar amounts of olefin and arylalkyl sulfonic acid. If very volatile or gaseous olefins are used the process may be carried out at elevated pressures.

The uniqueness of the reaction is that the arylalkyl sulfonic acids serves as the catalyst as well as one of the reactants for the formation of the polyalkylated arylalkyl sulfonic acid. Without being bound by any particular theory we believe that the presence of the sulfonic acid group at the end of the alkyl chain strongly activates unoccupied positions on the ring making them amenable to addition by unsaturated compounds such as olefins.

The polyalkylated arylalkyl sulfonic acid can be further neutralized with base to make the sulfonate salts of the polyalkylated arylalkyl sulfonic acid. Such bases include, but are not limited to sodium hydroxide, sodium carbonate, potassium hydroxide, potassium carbonate, calcium hydroxide, magnesium hydroxide, ammonium hydroxide, or amines.

The light colored polyalkylated arylalkyl sulfonic acids and their salts have been found useful as surfactants for many applications including, but not limited to surfactants for laundry detergents, heavy duty cleaning, oil recovery, oilfield drilling and production, agricultural emulsifiers, pharmaceutical emulsifiers, metal treating, and cutting fluids. The products can be combined with other surfactants to form useful synergistic mixtures.

The process of the present invention for making lighter colored polyalkylated arylalkyl sulfonic acids offers many unique advantages over the existing processes for manufacturing polyalkylaromatic sulfonic acids and their sulfonates as shown below:

(1) Useful light colored polyalkylated arylalkyl sulfonic acids and their sulfonates of different molecular weights can be made easily and economically as first intent products.

(2) The starting reactant arylalkyl sulfonic acid is also an effective catalyst so additional catalyst is not required.

(3) The polyalkylated arylalkyl sulfonic acid is made by alkylating the arylalkyl sulfonic acid with olefin and the process does not require the heavy alkylaromatic (heavy alkylate) precursor to be sulfonated.

(4) As is know to those familiar with the art, the thin film sulfonation process used to sulfonate alkylates is limited to lower viscosity and low molecular weight alkylates. Higher viscosity an/or higher molecular weight alkylates may cause poor conversion, plugging and fouling of the sulfonation equipment. The process of this invention uses the thin film sulfonation unit to produce the low molecular weight, low viscosity olefin sulfonic acids, which are further processed outside the sulfonation unit to form the final products.

(5) The process of the present invention does not require the conventional expensive alkylation process and catalyst to produce light color arylalkyl sulfonates that provides the surfactant properties for different industries. This eliminates the cost of building and maintaining an alkylation plant to produce alkylate. This also eliminates the need for toxic and expensive catalysts such as aluminum chloride or hydrofluoric acid that are used in such plants.

(6) The process produces light colored, low sulfate, high molecular weight sulfonic acids and salts suitable for applications where color and excess sulfate are of concern.

EXAMPLE 1

184 grams of a dialkyl, mono sulfonic acid were prepared by the method described previously by reacting 78.4 g (0.4 moles) 1-tetradecene with (0.2 moles) 16.0 g sulfur trioxide in a laboratory falling film reactor. The resulting 0.2 moles tetradecene olefin sulfonic acid contains 0.2 moles of excess, unreacted 1-tetradecene. This mixture was slowly added to 23.3 g (0.2 moles) xylene previously heated to 130° C. The material was allowed to react and additional 3.5 hours at 130° C. after which it was analyzed for residual 1-tetradecene by Gas Liquid Chromatography and for anionic activity by CID two-phase titration. Residual tetradecene was found to be 2.2% by weight and anionic activity was 97.8% by weight by potentiometric titration with methanolic cyclohexylamine in iso-propanol with no detectable sulfuric acid. The 5% Klett color of the material was 22 compared to 350 for the 5% Klett color for an acid prepared by the reaction described in U.S. patent application Ser. No. 11/895,497.

The invention and the manner and process of making and using it, are now described in such full, clear, concise and exact terms as to enable any person skilled in the art to which it pertains, to make and use same. It is to be understood that the foregoing describes preferred embodiments of the present invention and that modifications may be made therein depending from the spirit and scope of the present invention as set forth in the claims.

The invention claimed is:

1. A process for the manufacture of light color polyalkylated arylalkyl sulfonic acids and their salts comprising:
    a. sulfonating an olefin in the presence of excess olefin,
    b. further reacting the olefin sulfonic acid formed with an aromatic or substituted aromatic to form an arylalkyl sulfonic acid,
    c. allowing the arylalkyl sulfonic acid to further react with the excess olefin present to form polyalkylated arylalkyl sulfonic acid with the structure below

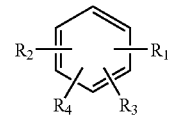

Where
$R_1$, $R_2$ and $R_3$ are each separately and independently H, alkyl (branched or linear C1 to C30),
$R_4=CH_3(CH_2)oCH(CH_2)pCH_3$
m+n=4 to 28
o+p=3 to 27,
    d. optionally neutralizing the polyalkylated arylalkyl sulfonic acid with a base.

2. The process for the manufacture of light color polyalkylated arylalkyl sulfonic acids and their salts of claim 1 where the olefin is an alpha olefin having 6 to 30 carbons.

3. The process for the manufacture of light color polyalkylated arylalkyl sulfonic acids and their salts of claim 1 where the olefin is an internal olefin having 4 to 30 carbons.

4. The process for the manufacture of light color polyalkylated arylalkyl sulfonic acids and their salts of claim 1 where the reaction is carried out at temperatures between 40° C. and 200° C.

5. The process for the manufacture of light color polyalkylated arylalkyl sulfonic acids and their salts of claim 1 where the reaction is carried out at atmospheric pressures.

6. The process for the manufacture of light color polyalkylated arylalkyl sulfonic acids and their salts of claim 1 where the reaction is carried out at elevated pressures.

7. The process for the manufacture of light color polyalkylated arylalkyl sulfonic acids and their salts of claim 1 where the polyalkylated arylalkyl sulfonic acid formed is neutralized with a base.

8. The process for the manufacture of light color polyalkylated arylalkyl sulfonic acids and their salts of claim 1 where the polyalkylated aryl alkyl sulfonic acid formed is neutralized with an base selected from the group: sodium hydroxide, sodium carbonate, potassium hydroxide, potassium carbonate, calcium hydroxide, magnesium hydroxide, ammonium hydroxide, amine.

* * * * *